United States Patent
Greten et al.

(10) Patent No.: US 7,985,773 B2
(45) Date of Patent: Jul. 26, 2011

(54) ENHANCED ACTIVITY ALCOHOL-BASED ANTIMICROBIAL COMPOSITIONS

(75) Inventors: Zachariah C. Greten, Shiloh, IL (US); Nancy-Hope E. Kaiser, Pontoon Beach, IL (US); Daniel A. Klein, Shiloh, IL (US)

(73) Assignee: American Sterilizer Company, Mentor, OH (US)

( * ) Notice: Subject to any disclaimer, the term of this patent is extended or adjusted under 35 U.S.C. 154(b) by 907 days.

(21) Appl. No.: 11/804,107

(22) Filed: May 17, 2007

(65) Prior Publication Data

US 2007/0219273 A1  Sep. 20, 2007

Related U.S. Application Data

(63) Continuation of application No. 10/922,456, filed on Aug. 20, 2004, now Pat. No. 7,268,165.

(51) Int. Cl.
*A01N 37/44* (2006.01)
*A01N 37/20* (2006.01)

(52) U.S. Cl. ........ 514/551; 424/405; 424/406; 514/613; 514/642; 514/724; 514/730

(58) Field of Classification Search .................. None
See application file for complete search history.

(56) References Cited

U.S. PATENT DOCUMENTS

| | | | |
|---|---|---|---|
| 5,288,486 A | 2/1994 | White | |
| 5,635,462 A | 6/1997 | Fendler et al. | |
| 5,939,082 A * | 8/1999 | Oblong et al. | ............... 424/401 |
| 5,997,893 A | 12/1999 | Jampani et al. | |
| 6,022,551 A | 2/2000 | Jampani et al. | |
| 6,024,951 A | 2/2000 | Babinski et al. | |
| 6,136,771 A | 10/2000 | Taylor et al. | |
| 6,183,766 B1 | 2/2001 | Sine et al. | |
| 6,228,385 B1 | 5/2001 | Shick | |
| 6,294,186 B1 * | 9/2001 | Beerse et al. | ............... 424/405 |
| 6,342,537 B1 | 1/2002 | Thomsen et al. | |
| 6,423,329 B1 | 7/2002 | Sine et al. | |
| 6,488,948 B1 | 12/2002 | Danieli | |
| 6,616,922 B2 | 9/2003 | Taylor et al. | |
| 6,723,689 B1 | 4/2004 | Hoang et al. | |
| 6,726,460 B2 | 4/2004 | Bailey et al. | |
| 6,846,846 B2 | 1/2005 | Modak et al. | |
| 7,192,601 B2 | 3/2007 | Walker | |
| 2004/0029758 A1 | 2/2004 | Yoshida et al. | |

FOREIGN PATENT DOCUMENTS

| | | |
|---|---|---|
| EP | 0414309 | 2/1991 |
| EP | 0 487 262 A2 | 5/1992 |
| EP | 1134279 | 9/2001 |
| FR | 1583994 | 12/1969 |
| WO | WO 01/41567 | 6/2001 |
| WO | WO 03/034994 | 5/2003 |

* cited by examiner

*Primary Examiner* — Neil Levy
(74) *Attorney, Agent, or Firm* — Hudak, Shunk & Farine Co. LPA

(57) ABSTRACT

Antimicrobial compositions which can be used wherever disinfecting compositions are needed, such as in a hospital, healthcare industry, workplace, recreational facility, home or similar environment. The antimicrobial compositions are particularly useful as a topical application for a substrate, such as skin and can be used as a hand sanitizer or pre-surgical scrub. The compositions comprise a synergistic combination of a simple aliphatic alcohol and an activity enhancing substance, wherein the composition provides, heretofore unexpected, persistent activity against a broad range of microorganisms, including gram-negative organisms, while moisturizing the skin.

20 Claims, 2 Drawing Sheets

ENHANCED ACTIVITY ALCOHOL-BASED ANTIMICROBIAL COMPOSITIONS

CROSS REFERENCE

This application is a continuation of application Ser. No. 10/922,456, filed on Aug. 20, 2004 now U.S. Pat. No. 7,268, 165, of Zachariah C. Greten et al., herein fully incorporated by reference.

FIELD OF THE INVENTION

The present invention relates to antimicrobial compositions which can be used wherever disinfecting compositions are needed, such as in a hospital, healthcare industry, workplace, recreational facility, home or similar environment. The antimicrobial compositions are particularly useful as a topical application for a substrate, such as skin and can be used as a hand sanitizer or pre-surgical scrub. The compositions comprise a synergistic combination of a simple aliphatic alcohol and an activity enhancing substance, wherein the composition provides, heretofore unexpected, persistent activity against a broad range of microorganisms, including gramnegative organisms, while moisturizing the skin.

BACKGROUND OF THE INVENTION

Various forms of antimicrobial compositions containing alcohols are known in the art and have been used in the healthcare industry for some time. The antimicrobial compositions are typically utilized to cleanse the skin and destroy bacteria and other microorganisms present thereon, especially on the hands, arms, and face of the user.

An important use of the antimicrobial composition is to disinfect the hands and fingers of a person. The composition is generally applied to, and rubbed into the hands and fingers, and subsequently allowed to evaporate from the skin. Wiping of the composition from the skin is typically not necessary because of the alcohol content of the compositions which leads to fast and essentially complete evaporation of the composition from the skin.

Antimicrobial compositions in general have been used in the healthcare industry, food service industry, meat processing industry, and in the private sector by individual consumers to control and prevent the spread of potentially harmful microorganisms. The widespread use of antibacterial compositions indicates the importance of controlling bacteria and other microorganism populations on the skin or other substrates. It is important, that the antimicrobial compositions reduce microorganism populations rapidly, without irritating or damaging skin or having a detrimental toxicity. The prior art antimicrobial compositions generally contain a high percentage of alcohol, wherein the alcohol acts as a disinfectant which rapidly evaporates preventing the need to wipe or rinse the composition from the treated surface. However, it has been found that high amounts of alcohol generally greater than about 60% dry and/or irritate skin.

U.S. Pat. No. 5,288,486 relates to a process for enhancing the efficacy of alcohol-based skin antiseptics comprising adding at least one alcohol-soluble viscosifying agent to an alcohol-based disinfectant, thereby lowering its alcohol evaporation rate and markedly increasing the exposure time that disinfecting concentrations of alcohol are present on skin.

U.S. Pat. No. 5,635,462 relates to a reportedly cleansing composition including a substituted phenol such as para-chloro-meta-xylenol, and at least one primary surfactant selected from the group consisting of amine oxides, phospholipids, partially neutralized carboxylic acids and diacids, betaines, ethoxylated methyglucosides, and mixtures thereof. Other additives such as viscosifiers or thickeners, emollients, fragrances, perfumes, coloring agents, and the like may also be added.

U.S. Pat. No. 5,997,893 relates to reportedly antimicrobial compositions containing high levels of alcohol, carbomer polymers and antimicrobial agents which provide formulations possessing cosmetic characteristics.

U.S. Pat. No. 6,022,551 relates to reportedly antimicrobial alcohol-containing composition and method of using the composition to reportedly disinfect surfaces, such as the hands is disclosed.

U.S. Pat. No. 6,136,771 relates to reportedly antibacterial compositions having a reduced amount of disinfecting alcohol. The antibacterial compositions contain a phenolic antibacterial agent, a disinfecting alcohol, a gelling agent, and water, wherein a percent saturation of the antibacterial agent in a continuous aqueous phase of the composition is at least 25%.

U.S. Pat. No. 6,228,385 relates to a liquid reportedly antimicrobial, skin moisturizing formulation including: 1) an aqueous alcoholic base; 2) a humectant; 3) a delivery material adapted to release an emollient when the formulation is applied to the skin; and 4) an emollient immiscible in the aqueous alcoholic base and contained by the delivery material. The delivery material reportedly encapsulates or entraps the emollient for subsequent release. Desirably, the humectant is glycerin and the emollient is an alkyl-substituted polysiloxane polymer.

U.S. Pat. No. 6,423,329 relates to compositions and methods of sanitizing and moisturizing skin surfaces.

U.S. Pat. No. 6,723,689 relates to a reportedly antimicrobial composition comprising an alcohol in an amount from about 60 to about 95 weight percent of the total composition, a preservative, a cationic cellulose polymer thickening agent, a moisturizer and/or a cationic emulsifier, and water in an amount from about 6 to about 30 weight percent.

A need exists for antimicrobial compositions which are effective against a broad spectrum of microorganisms including gram positive and gram negative bacteria and provide enhanced antimicrobial activity and thus provide a longer period of protection for the user.

SUMMARY OF THE INVENTION

Antimicrobial compositions are disclosed which provide enhanced or prolonged activity against various microorganisms. The aliphatic alcohol concentration of the compositions is kept at a moderate level in order to prevent irritation to skin. It has been unexpectedly found that activity enhancing substances synergistically combine with the aliphatic alcohol in the compositions of the present invention to provide residual activity on a substrate and prevent subsequent microorganism growth when compared to alcohol alone. It is believed that the compositions retard evaporation of the alcohol and/or other antimicrobial agent if present, and increasing the contact time with the substrate i.e., skin being treated; or bind with the skin and remain on the surface thereby maintaining effectiveness against subsequent contact with a microorganism; or combinations thereof.

The antimicrobial compositions comprise an aliphatic alcohol, preferably in an amount of about 50 to about 58 parts by weight, one or more activity enhancing substances in a range from about 0.0125 to about 10 parts by weight, and water based on 100 parts by weight of the antimicrobial composition. The compositions can optionally include other components including, but not limited to, humectants, skin conditioners, emollients, viscosifying agents, preservatives, and fragrances.

BRIEF DESCRIPTION OF THE DRAWINGS

The invention will be better understood and other features and advantages will become apparent by reading the detailed description of the invention, taken together with the drawings, wherein.

DETAILED DESCRIPTION OF THE INVENTION

Figure 1:
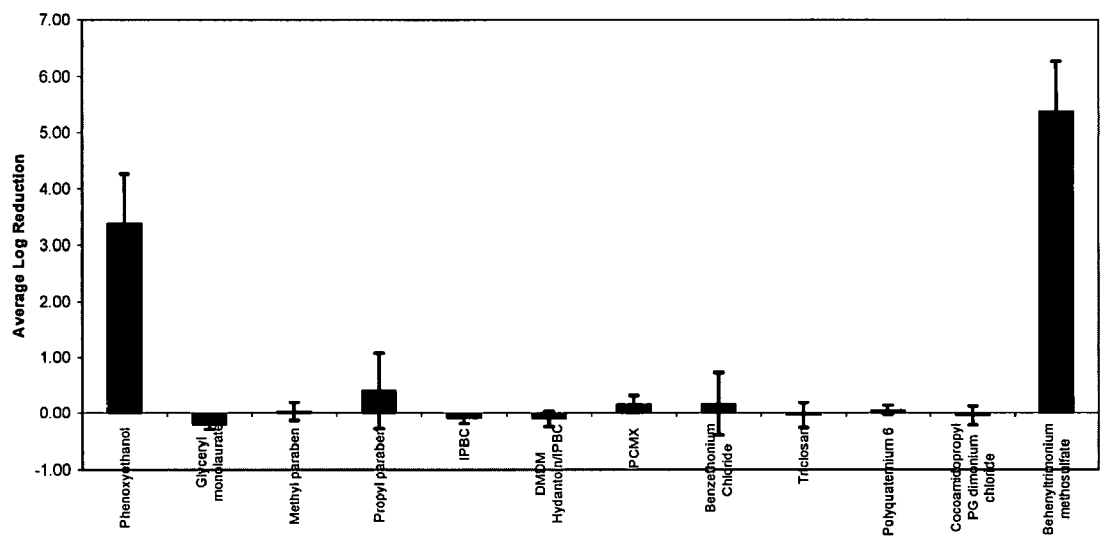
FIG. 1 illustrates residual activity values in average log reduction of compositions containing various additives.

The present invention is directed to enhanced activity alcohol-based antimicrobial compositions which are preferably utilized as skin disinfectants or antiseptics which provide the skin or other surface with prolonged antimicrobial properties. Methods for preparing antimicrobial compositions are also described.

Alcohol-containing or alcohol-based antimicrobial compositions are typically drying and even irritating to the skin, especially when utilized repeatedly as required in the healthcare field. While searching for components which could increase the moisturizing capabilities of an alcohol-based composition, it was unexpectedly discovered that compositions could be formulated comprising an aliphatic alcohol and an activity enhancing substance, which exceeded the activity of a composition without the latter component. In most cases, the moisturizing ability of the compositions are improved in addition to providing increased activity of the composition against microorganisms.

The compositions of the present invention include an aliphatic alcohol which has inherent antiseptic properties. Such alcohols are known to kill various viruses, fungi, mold, and gram positive and gram negative bacteria. Suitable alcohols are short chain, linear or branched, aliphatic alcohols, and generally have from 1 to about 8 carbon atoms with 1 to about 4 carbon atoms being preferred. Examples include, but are not limited to, methanol, ethanol, n-propanol, isopropyl alcohol, 2-methyl-2 propanol and hexanol, or combinations thereof. Propanol, isopropyl alcohol and ethanol are preferred.

The aliphatic alcohol is present in a range generally from 30 parts to about 90 parts, desirably from about 45 parts to less than about 60 parts, and preferably from about 50 parts to about 57 or 58 parts by weight per 100 parts by weight of the composition. It has been unexpectedly found that compositions having less than 60 parts aliphatic alcohol can be effective antimicrobials having enhanced activity.

The alcohol is combined with an activity enhancing substance which increases the residual activity of the composition and beneficially the effectiveness of the antibacterial activity as indicated by a log reduction in microorganisms. Typical prior art antibacterial compositions generally offer a low to moderate antibacterial activity. Antibacterial activity is assessed against a broad spectrum of microorganisms, including both gram positive and gram negative bacteria. Log reduction or alternatively percent reduction, in bacterial populations provided by the composition correlates to antibacterial activity. Log reductions on skin of between one and three are desired, and log reductions greater than three are preferred for a particular contact time which generally ranges from 15 seconds to about 5 minutes.

The activity enhancing substance can generally be classified as one of two types, an aromatic alcohol activity enhancing substance, or a cationic substrate binding activity enhancing substance. One or preferably both types of activity enhancing substances are utilized in the compositions of the present invention. Suitable cationic substrate binding activity enhancing substances include, but are not limited to, behentrimonium methosulfate, behenalkonium chloride, behenoyl PG-trimonium chloride, behenoyl PG-dimonium chloride, behenamidopropyl PG-dimonium chloride, or combinations thereof. The cationic substrate binding activity enhancing substances are utilized in the antimicrobial compositions in amounts which range generally from about 0.0125 to about 0.50 parts, desirably from about 0.03 to about 0.10 parts, and preferably from about 0.04 to about 0.075 parts based on 100 parts by weight of the composition. Some of the substrate binding activity enhancing substances are commercially available as blends at various concentrations. Often, the substrate binding activity enhancing substances are blended with one or more long chain aliphatic alcohols having greater than about 10 carbon atoms such as, but not limited to, cetyl alcohol, stearyl alcohol, behenyl alcohol or cetearyl alcohol which is generally a 50/50 mixture by weight of cetyl and stearyl alcohol.

The aromatic alcohol activity enhancing substances include at least one phenyl group and an alcohol functional group indirectly attached to the phenyl ring, for example wherein the hydroxyl group of the aromatic alcohol is connected to a non-aromatic ring carbon atom, such as through aliphatic linkage or ether linkage, for example. Suitable aromatic alcohol activity enhancing substances include, but are not limited to, phenoxyethanol, 1-phenoxy 2-propanol, and benzyl alcohol. The aromatic alcohol activity enhancing substances are utilized in the antimicrobial compositions in amounts which range generally from about 0.5 to about 5.0, desirably from about 0.75 to about 3.5, and preferably from about 1.0 to about 2.5 parts based on 100 parts by weight of the composition.

Polyols are optionally but preferably utilized in the antimicrobial compositions of the present invention. Polyols contain from 2 to about 6 and desirably 2 or 3 hydroxyl groups. Preferred polyols are water soluble. The polyols utilized in the present invention are typically skin conditioners such as humectants or moisturizers. Specific examples of polyols include, but are not limited to, ethylene glycol, propylene glycol, glycerol, diethylene glycol, triethylene glycol, dipropylene glycol, tripropylene glycol, hexylene glycol, butylene glycol, 1,2,6-hexanetriol, sorbitol, PEG-4 and similar polyhydroxy compounds, and 2-methyl-1,3-propane diol.

In addition to the polyols, the antimicrobial compositions of the present invention can include other skin conditioners such as humectants, emollients, moisturizers or the like. Emollients are generally thin liquids, oils of various viscosities, fatty solids or waxes. A function of the skin conditioner is to soften and soothe the skin and to prevent chapping of the same. Preferably the skin conditioner chosen does not leave a tacky feel on the skin. Examples of such compounds include, but are not limited to, cyclomethicone, cetyl myristate, glyceryl dioleate, isopropyl myristate, lanolin, methyl laurate, PPG-9 laurate, soy stearyl, octyl palmitate, Di-PPG-3 myristyl ether adipate, C12-C15 alkyl benzoates, PPG-5 lanoate, glucamine and pyridoxine glycol, for example. Occlusive skin conditioners, for example, cetyl lactate, aluminum lanolate, corn oil, dimethicone, coconut oil, stearyl stearate, phenyl trimethicone, trimyristin, olive oil, and synthetic wax, also can be used. Combinations of the classes of skin conditioners, in addition to miscellaneous skin conditioners known to persons skilled in the art, alone or in combination can be used. Nonlimiting examples of miscellaneous skin conditioners include aloe, cholesterol, cystine, keratin, lecithin, egg yolk, glycine, PPG-12, retinol, salicylic acid, orotic acid, vegetable oil, and soluble animal collagen. The skin conditioners can be used alone, or in combination with a skin protectant, like petroleum, cocoa butter, calamine, and kaolin, for example.

Still other skin conditioners include alcohol soluble polyquaterniums, including but not limited to, Merquat 100, which is N,N-dimethyl-N-2-propen-1-aminium chloride, polyquaternium 22 (acrylic acid-diallyldimethylammonium chloride polymer) and polyquaternium 47 (1-propanaminium,N,N,N-trimethyl-3-((2-methyl-1-oxo-2-propenyl) amino)-chloride polymer with methyl 2-propenoate and 2-propenoic acid), all commercially available from ONDEO Nalco of Naperville, Ill.

One or more skin conditioners, emollients, humectants, or the like can be utilized in the antimicrobial compositions of the present invention in total amounts which range generally from about 0.25 to about 10 parts, desirably from about 0.50 to about 5.0 parts, and preferably from about 1.0 to about 3.5 parts based on 100 parts by weight of the composition.

Thickening agents are optionally but preferably utilized in the antimicrobial compositions of the present invention in order to increase the viscosity thereof. Thickening compounds can be both organic and inorganic. The antimicrobial compositions of the present invention can be a liquid but typically contain a sufficient amount of a thickening agent such that the composition is a viscous liquid or flowable gel that can be easily applied to a substrate such as skin. The type and amount of thickeners utilized in the composition depend upon the desired viscosity thereof among other factors. That said, a thickener, when utilized in the present invention, is present in a range generally from about 0.1 to about 3.0 parts, desirably from about 0.15 to about 1.0 part, and preferably from about 0.2 to about 0.75 parts based on 100 parts by weight of the composition.

The compositions of the present invention have viscosities which range generally from about 10 to 100,000 centipoise (cp), desirably from about 30 to about 5,000 centipoise (cp), and preferably from about 60 to about 120 centipoise (cp) as measured using a low shear viscosity determination method such as the helipath method using an inverted "t" spindle as known in the art (Brookfield Method).

Various thickeners can be utilized to thicken the aqueous and/or non-aqueous portion of the antimicrobial composition. Examples of suitable thickeners include, but are not limited to, acacia, acrylates/steareth-20 methacrylate copolymer, agar, algin, alginic acid, ammonium acrylate copolymers, ammonium alginate, ammonium chloride, ammonium sulfate, amylopectin, attapulgite, bentonite, C9-15 alcohols, calcium acetate, calcium alginate, calcium carrageenan, calcium chloride, caprylic alcohol, carbomer 910, carbomer 934, carbomer 934P, carbomer 940, carbomer 941, carboxymethyl hydroxyethylcellulose, carboxymethyl hydroxypropyl guar, carrageenan, cellulose, cellulose gum, cetearyl alcohol, cetyl alcohol, corn starch, damar, dextrin, dibenzylidine sorbitol, ethylene dihydrogenated tallowamide, ethylene dioleamide, ethylene distearamide, gelatin, guar gum, is guar hydroxypropyltrimonium chloride, hectorite, hyaluronic acid, hydrated silica, hydroxybutyl methylcellulose, hydroxyethylcellulose, hydroxyethyl ethylcellulose, hydroxyethyl stearamide-MIPA, hydroxypropylcellulose, 2-hydroxypropyl ether cellulose, hydroxypropyl guar, hydroxypropyl methylcellulose, isocetyl alcohol, isostearyl alcohol, karaya gum, kelp, lauryl alcohol, locust bean gum, magnesium aluminum silicate, magnesium silicate, magnesium trisilicate, methoxy PEG-22/dodecyl glycol copolymer, methylcellulose, microcrystalline cellulose, montmorillonite, myristyl alcohol, oat flour, oleyl alcohol, palm kernel alcohol, pectin, PEG-2M, PEG-5M, polyacrylic acid, polyvinyl alcohol, potassium alginate, potassium aluminum polyacrylate, potassium carrageenan, potassium chloride, potassium sulfate, potato starch, propylene glycol alginate, sodium acrylate/vinyl alcohol copolymer, sodium carboxymethyl dextran, sodium carrageenan, sodium cellulose sulfate, sodium chloride, sodium polymethacrylate, sodium silicoaluminate, sodium sulfate, stearalkonium bentonite, stearalkonium hectorite, stearyl alcohol, tallow alcohol, TEA-hydrochloride, tragacanth gum, tridecyl alcohol, tromethamine magnesium aluminum silicate, wheat flour, wheat starch, xanthan gum, and mixtures thereof.

The following additional nonlimiting examples of thickening agents act primarily by thickening the nonaqueous portion of the composition: abietyl alcohol, acrylinoleic acid, aluminum behenate, aluminum caprylate, aluminum dilinoleate, aluminum distearate, aluminum isostearates/laurates/palmitates or stearates, aluminum isostearates/myristates, aluminum isostearates/palmitates, aluminum isostearates/stearates, aluminum lanolate, aluminum myristates/palmitates, aluminum stearate, aluminum stearates, aluminum tristearate, beeswax, behenamide, behenyl alcohol, butadiene/acrylonitrile copolymer, C29-70 acid, calcium behenate, calcium stearate, candelilla wax, carnauba, ceresin, cholesterol, cholesteryl hydroxystearate, coconut alcohol, copal, diglyceryl stearate malate, dihydroabietyl alcohol, dimethyl lauramine oleate, dodecanedioic acid/cetearyl alcohol/glycol copolymer, erucamide, ethylcellulose, glyceryl triacetyl hydroxystearate, glyceryl tri-acetyl ricinoleate, glycol dibehenate, glycol di-octanoate, glycol distearate, hexanediol distearate, hydrogenated C6-14 olefin polymers, hydrogenated castor oil, hydrogenated cottonseed oil, hydrogenated lard, hydrogenated menhaden oil, hydrogenated palm kernel glycerides, hydrogenated palm kernel oil, hydrogenated palm oil, hydrogenated polyisobutene, hydrogenated soybean oil, hydrogenated tallow amide, hydrogenated tallow glyceride, hydrogenated vegetable glyceride, hydrogenated vegetable glycerides, hydrogenated vegetable oil, hydroxypropylcellulose, isobutylene/isoprene copolymer, isocetyl stearoyl stearate, Japan wax, jojoba wax, lanolin alcohol, lauramide, methyl dehydroabietate, methyl hydrogenated rosinate, methyl rosinate, methylstyrene/vinyltoluene copolymer, microcrystalline wax, montan acid wax, montan wax, myristyleicosanol, myristyloctadecanol, octadecene/maleic anhydride copolymer, octyldodecyl stearoyl stearate, oleamide, oleostearine, ouricury wax, oxidized polyethylene, ozokerite, palm kernel alcohol, paraffin, pentaerythrityl hydrogenated rosinate, pentaerythrityl rosinate, pentaerythrityl tetraabietate, pentaerythrityl tetrabehenate, pentaerythrityl tetraoctanoate, pentaerythrityl tetraoleate, pentaerythrityl tetrastearate, phthalic anhydride/glycerin/glycidyl decanoate copolymer, phthalic/trimellitic/glycols copolymer, polybutene, polybutylene terephthalate, polydipentene, polyethylene, polyisobutene, polyisoprene, polyvinyl butyral, polyvinyl laurate, propylene glycol dicaprylate, propylene glycol dicocoate, propylene glycol diisononanoate, propylene glycol dilaurate, propylene glycol dipelargonate, propylene glycol distearate, propylene glycol diundecanoate, PVP/eicosene copolymer, PVP/hexadecene copolymer, rice bran wax, stearalkonium bentonite, stearalkonium hectorite, stearamide, stearamide DEA-distearate, stearamide DIBA-stearate, stearamide MEA-stearate, stearone, stearyl alcohol, stearyl erucamide, stearyl stearate, stearyl stearoyl stearate, synthetic beeswax, synthetic wax, trihydroxystearin, triisononanoin, triisostearin, triisononanoin, triisostearin, tri-isostearyl trilinoleate, trilaurin, trilinoleic acid, trilinolein, trimyristin, triolein, tripalmitin, tristearin, zinc laurate, zinc myristate, zinc neodecanoate, zinc rosinate, zinc stearate, and mixtures thereof.

In a preferred embodiment, the thickener utilized is a non-ionic thickener such as 2-hydroxypropyl ether cellulose available from Aqualon as Klucel HF. The compositions of the present invention are preferably free of both anionic and cationic thickening agents. The use of non-ionic thickeners provides broad compatibility with the wide range of formulation ingredients utilized. Antipodally, anionic or cationic thickeners can inactivate antimicrobial agents utilized in the compositions of the invention.

The antimicrobial compositions of the present invention utilize water, preferably deionized water, as a carrier. Water is utilized in a range generally from about 5 or 20 to about 65 parts, desirably from about 33 or 35 to about 50 parts, and preferably from about 37 to about 45 parts based on 100 parts by weight of the composition.

The compositions of the present invention optionally include a preservative component. Examples of suitable preservatives include, but are not limited to, chlorhexidine gluconate, chlorhexidine acetate, chlorhexidine isethionate, chloroxylenol, triclosan, methyl paraben, propyl paraben, butyl paraben, quaternium 15, DMDM hydantoin, iodopropynybutyl carbamate, diazolindinyl urea, imidazolidinyl urea, parachlormetaxylenol, chlorhexidine diacetate, glyceryl monolaurate, pyrithione (zinc, sodium, and MDS), 2-bromo-2-nitropropane-1,3-diol, chloroacetamide, triclocarban, propamidine isethionate, hexamidine isetnionate, hexetidine, polyhexamethylene biguanide hydrochloride, alkyltrimethylammonium bromide, benzalkonium chloride and benzethonium chloride. The preservative is utilized in the present invention in various amounts.

The antimicrobial compositions of the present invention can contain optional ingredients which include, but are not limited to, dyes, fragrances, pH adjusters, buffering agents, antioxidants, emulsifiers and surfactants. The optional ingredients can be utilized in various amounts to achieve a desired effect on the composition, as known to those of ordinary skill in the art. Examples of suitable dyes include, but are not limited to, D&C blue 1, D&C brown 1, D&C green 5, D&C green 6, D&C green 8, D&C orange 4, D&C orange 5, D&C orange 11, D&C orange 12, D&C red 6, D&C red 7, D&C red 17, D&C red 21 D&C red 27, D&C red 30, D&C red 33 D&C red 34, D&C red 36, D&C violet 2, D&C yellow 10, D&C yellow 11, D&C yellow 7, D&C yellow 8, FD&C blue 1, FD&C green 3, FD&C red 4, FD&C red 40, FD&C yellow 5, FD&C yellow 6, or any blend thereof.

The pH adjusters can be utilized if desired in order to impart the compositions of the present invention with a pH of about 4 to about 8, and preferably from about 4.5 to about 6, if the composition is not already within the noted ranges. The pH adjusters include, but are not limited to, ammonia, sodium hydroxide, potassium hydroxide, lithium hydroxide, ethanol amine, triethyl amine, isopropanol amine, diisopropanol amine, tromethamine, tetrahydroxy propyl ethylene diamine, isopropyl amine, diethanol amine, triethyanol amine, citric acid, glycolic acid, lactic acid, hydrochloric acid, nitric acid, phosphoric acid, salicylic acid, and sulfuric acid.

In some embodiments, additional antimicrobial compounds can be utilized in the compositions of the present invention. Suitable antimicrobials include, but are not limited to, benzalkonium chloride, benzethonium chloride, CHG or phenols, optionally substituted, such as triclosan, some of which as noted above, also have other functions such as being a preservative. In most embodiments however, the compositions of the present invention are free of such antimicrobials other than the aliphatic alcohol and activity enhancing substances.

The present invention will be better understood by reference to the following examples which serve to describe, but not to limit, the present invention.

Examples

Various compounds were tested in the aliphatic alcohol-based formulation set forth in Table I to determine if moisturization could be improved. It was unexpectedly discovered during experimentation that one of the components utilized, behentrimonium methosulfate enhanced activity of the alcohol composition against Serratia Marcescens ATCC 14756. Following this unexpected discovery, various other compounds, including quaternary ammonium compounds, were tested in the formulation of Table I to determine if any enhanced activity could also be observed. Testing showed that very few quaternary ammonium compounds offered substantial enhanced activity, whereas a majority of quaternary ammonium compounds show little or even a negative effect on antimicrobial activity.

TABLE I

| Component | Weight Percent |
| --- | --- |
| Deionized Water | 40.990 |
| Polyquaternum 6 | 0.480 |
| Cetyl lactate | 0.480 |
| Hydroxypropyl cellulose | 0.240 |
| Fragrance | 0.024 |
| Isopropyl alcohol | 53.850 |
| Methylpropanediol | 1.92 |
| Glycerin | 1.92 |
| $C_{12}$-$C_{15}$ alkyl benzoate (Finsolv TN) | 0.096 |
| Total | 100 |

Each component listed in Table II was separately added to the above alcohol-based formulation listed in Table I and tested to determine if antimicrobial activity could be enhanced. The weight percentages listed in Table II are based on 100 total parts by weight of the composition in Table I and the listed component. For example with Experiment A, 5 parts of phenoxyethanol was tested in 95 parts of the composition listed in Table I.

TABLE II

| Experiment | Additive Components | Weight % |
| --- | --- | --- |
| A | Phenoxyethanol (ethylene glycol phenyl ether) (90%) | 5 |
| B | Glyceryl monolaurate (Lauricidin) | 1 |
| C | Methyl paraben | 0.2 |
| D | Propyl paraben | 0.1 |
| E | Iodopropynyl butylcarbamate | 0.15 |
| F | Glydant plus (DMDM Hydantoin/IPBC) | 0.08 |
| G | PCMX | 0.125 |
| H | Benzethonium chloride | 0.13 |
| I | Triclosan | 0.10 |
| J | Polyquaternium 6 (40%) | 0.50 |
| K | Cocoamidopropyl PG dimonium chloride (40%) | 2.0 |
| L | Behentrimonium methosulfate in cetearyl alcohol at 25% concentrate | 0.50 |

The following procedure was utilized to prepare the example formulations. The appropriate amount of water was heated to a temperature sufficient to dissolve any solid components, such as from about 70° C. to about 80° C. for behentrimonium methosulfate. The solid components such as behentrimonium methyosulfate were added to the water with mixing utilizing an impeller mixer. The solution was subsequently cooled to a temperature of about 60° wherein hydroxypropyl cellulose was added with mixing. The solution was further cooled to allow the polymer to hydrate. The cetyl lactate, polyquaternium-6, glycerin, methylpropanediol, phenoxyethanol (in the case of experiment A) or other noted additive in Table II, and fragrance were added, preferably sequentially with mixing appropriate to disperse the materials. If necessary, additional water was added to replace water lost during processing as determined by appropriate vessel gross and net weights. Next, the appropriate aliphatic alcohol, such as isopropanol, was added with mixing to complete the composition. It is to be understood that variations of the above-described process can be utilized. For example, multitank processes can be utilized, and/or various types of dispersing equipment can replace the higher temperature dispersion of some components, etc.

Residual Activity Testing Procedure: Each formulation was tested on pigskin to evaluate the effect of the compositions on a gram negative organism, *Serratia marcescens* ATCC 14756. The gram negative organism was grown for approximately 24 hours at 30° C. and then suspended in Butterfields Buffer to a count of $1 \times 10^8$. The pigskins were prepared according to the following standard of procedure. Pigskin hides are collected on the date of slaughter and processed on the same day by removing adipose tissue and thoroughly cleaning the hide. Both of these processes are accomplished by spraying both sides of the pig hide with a high pressure washer. No soap or detergents are used at any time during the processing of pig hides for laboratory use. After cleaning and de-fatting, pigskins are placed in water and frozen at the farm from which they were harvested. When required for laboratory testing, a representative procures the hides and thaws them for laboratory manipulation. In the laboratory, these hides are cut into manageable pieces with a scalpel and coarse hair removed with animal grooming clippers. Disposable razors are further employed to create a smooth surface without negatively affecting the skin surface. These pieces are then sterilized by Gamma irradiation and kept frozen until use in a study. Testing circles were then punched out of the pigskins and glued to a phenolic cap. The testing samples were placed in a 30° C. oven to equilibrate for at least 20 minutes. Each skin was treated with 150 µl of test product and rubbed for 30 seconds as a pair, skin to skin. The skins were allowed to dry for 30 seconds and then the test product was reapplied four times in the same manner. The skins were allowed to dry in a slightly opened hood for 15 minutes. After drying the skins were inoculated with 31 µl of the *Serratia marcescens* inoculum, as prepared above, rubbed for 15 seconds, and sampled after three minutes. To sample, a sterile 3.5 cm diameter cylinder is placed, lip side down, over the pigskin on the cap. Enough pressure is applied to the cylinder to prevent any leakage upon the addition of an appropriate volume of liquid sampling solution to the cylinder. The skin is then debrided, using a sterile policeman, for 30 seconds by rubbing the surface of the skin with the flat edge of the policeman with enough pressure to remove any microorganisms that might be on the surface. Two mL of the sampling solution are removed using a sterile pipet and are utilized for preparing serial dilutions and aerobic plate counts to establish the number of Colony Forming Units remaining.

FIG. 1 illustrates in average log reduction residual activity results of the testing procedure described above. The quaternary ammonium compound behentrimonium methosulfate and phenoxyethanol exhibited enhanced antimicrobial activity when compared to the remaining components listed in Table II.

FIG. 1 was derived from the following data which was gathered utilizing the above described residual activity testing procedure.

TABLE III

| Series | Test Product (active %) | Log Reduction | Average Log Reduction | Average Series |
|---|---|---|---|---|
| 1 | Phenoxyethanol (5%) | 3.93 | 3.06 | 3.39 |
| 2 | Phenoxyethanol | 2.19 | | |
| 3 | Phenoxyethanol | 4.13 | 3.72 | |
| 4 | Phenoxyethanol | 3.30 | | |
| 5 | Glyceryl monolaurate (1%) | −0.29 | −0.23 | −0.21 |
| 6 | Glyceryl monolaurate | −0.17 | | |
| 7 | Glyceryl monolaurate | −0.10 | −0.18 | |
| 8 | Glyceryl monolaurate | −0.26 | | |
| 9 | Methyl paraben (0.2%) | −0.16 | −0.11 | 0.03 |
| 10 | Methyl paraben | −0.06 | | |
| 11 | Methyl paraben | 0.16 | 0.17 | |
| 12 | Methyl paraben | 0.18 | | |
| 13 | Propyl paraben (0.1%) | 1.38 | 0.85 | 0.40 |
| 14 | Propyl paraben | 0.33 | | |
| 15 | Propyl paraben | 0.01 | −0.05 | |
| 16 | Propyl paraben | −0.12 | | |
| 17 | IPBC (0.015%) | −0.22 | −0.15 | −0.10 |
| 18 | IPBC | −0.07 | | |
| 19 | IPBC | −0.02 | −0.05 | |
| 20 | IPBC | −0.08 | | |
| 21 | DMDM Hydantoin/IPBC (0.08%) | 0.01 | 0.00 | −0.10 |
| 22 | DMDM Hydantoin/IPBC | −0.02 | | |
| 23 | DMDM Hydantoin/IPBC | −0.11 | −0.21 | |
| 24 | DMDM Hydantoin/IPBC | −0.30 | | |
| 25 | PCMX (0.125%) | 0.18 | 0.06 | 0.16 |
| 26 | PCMX | −0.07 | | |
| 27 | PCMX | 0.26 | 0.26 | |
| 28 | PCMX | 0.26 | | |
| 29 | Benzethonium Chloride (0.13%) | 0.03 | 0.51 | 0.17 |
| 30 | Benzethonium Chloride | 0.98 | | |
| 31 | Benzethonium Chloride | −0.32 | −0.17 | |
| 32 | Benzethonium Chloride | −0.01 | | |
| 33 | Triclosan (0.1%) | −0.22 | −0.23 | −0.04 |
| 34 | Triclosan | −0.24 | | |
| 35 | Triclosan | 0.13 | 0.15 | |
| 36 | Triclosan | 0.18 | | |
| 37 | Polyquaternium 6 (0.2%) | 0.05 | 0.04 | 0.05 |
| 38 | Polyquaternium 6 | 0.04 | | |
| 39 | Polyquaternium 6 | 0.17 | 0.07 | |
| 40 | Polyquaternium 6 | −0.03 | | |
| 41 | Cocoamidopropyl PG dimonium chloride (0.8%) | −0.06 | −0.13 | −0.04 |
| 42 | Cocoamidopropyl PG dimonium chloride | −0.21 | | |
| 43 | Cocoamidopropyl PG dimonium chloride | −0.10 | 0.04 | |
| 44 | Cocoamidopropyl PG dimonium chloride | 0.19 | | |
| 45 | Behentrimonium methosulfate (0.125%) | 5.83 | 4.94 | 5.39 |
| 46 | Behentrimonium methosulfate | 4.05 | | |
| 47 | Behentrimonium methosulfate | 5.83 | 5.83 | |
| 48 | Behentrimonium methosulfate | 5.83 | | |

Figure 2:
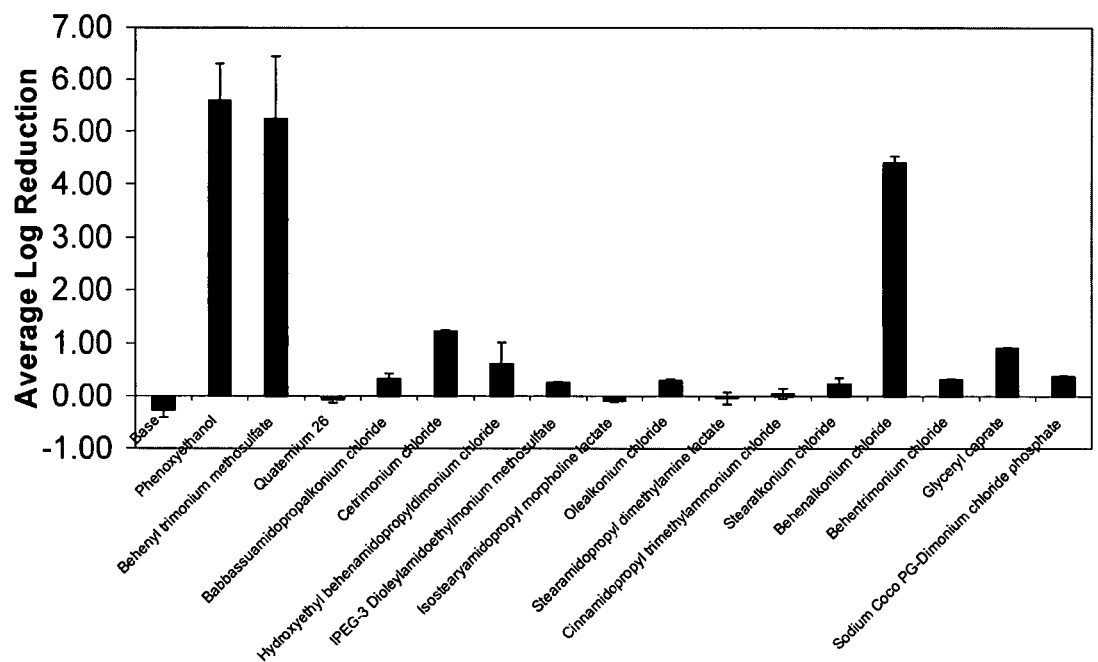
FIG. 2 illustrates additional residual activity values in average log reduction of compositions containing various additives.

After it was unexpectedly discovered that the quaternary ammonium compound behentrimonium methosulfate provided increased antimicrobial activity in the base formulation, additional quaternary ammonium compounds were screened to determine their effectiveness, if any. The same formulation utilized in Table I was utilized as the base formulation for testing purposes. The various quaternary ammonium compounds listed in Table V were added to the base formulation at a rate of 0.5 parts by weight per 100 parts total composition. The base formulation and formulations including each quaternary ammonium compound were tested utilizing the residual activity test procedure described hereinabove. The results of the experiments are also listed in FIG. 2 and in Table V.

TABLE IV

| Additive Component | Weight % |
|---|---|
| Phenoxyethanol | 0.5 |
| Behentrimonium Methosulfate in cetearyl alcohol at 25% concentration | 0.5 |
| Quaternium 26 | 0.5 |
| Babbassuamidopropalkonium Chloride | 0.5 |
| Centrimonium Chloride | 0.5 |
| Hydroxyethyl behenamidopropyldimonium chloride | 0.5 |
| Dioleylamidoethylmonium methosulfate, propylene glycol | 0.5 |
| Isostearyamidopropyl morpholine lactate | 0.5 |
| Olealkonium Chloride | 0.5 |
| Stearamidopropyl dimethylamine lactate | 0.5 |
| Cinnamidopropyl trimethylammonium chloride | 0.5 |
| Stearalkonium chloride | 0.5 |
| Behenalkonium Chloride | 0.5 |
| Glyceryl caprate | 0.5 |
| Sodium Coco PG-Dimonium chloride phosphate | 0.5 |

TABLE V

| Series | Test Product | Log Value | Log Reduction | Average Log Reduction |
|---|---|---|---|---|
| 1 | Base | 6.28 | −0.18 | −0.27 |
| 2 | Base | 6.46 | −0.36 | |
| 3 | Phenoxyethanol | 1.00 | 5.10 | 5.60 |
| 4 | Phenoxyethanol | 0.00 | 6.10 | |
| 5 | Behentrimonium methosulfate | 0.00 | 6.10 | 5.25 |
| 6 | Behentrimonium methosulfate | 1.70 | 4.40 | |
| 7 | Quaternium 26 | 6.20 | −0.11 | −0.07 |
| 8 | Quaternium 26 | 6.13 | −0.03 | |
| 9 | Babbassuamidopropalkonium chloride | 5.82 | 0.28 | 0.35 |
| 10 | Babbassuamidopropalkonium chloride | 5.68 | 0.42 | |
| 11 | Cetrimonium chloride | 4.87 | 1.23 | 1.24 |
| 12 | Cetrimonium chloride | 4.85 | 1.25 | |
| 13 | Hydroxyethyl behenamidopropyl-dimonium chloride | 5.19 | 0.91 | 0.63 |
| 14 | Hydroxyethyl behenamidopropyl-dimonium chloride | 5.75 | 0.35 | |
| 15 | IPEG-3 Dioleylamidoethylmonium methosulfate | 5.84 | 0.26 | 0.27 |
| 16 | IPEG-3 Dioleylamidoethylmonium methosulfate | 5.81 | 0.29 | |
| 17 | Isostearyamidopropyl morpholine lactate | 6.17 | −0.07 | −0.09 |
| 18 | Isostearyamidopropyl morpholine lactate | 6.20 | −0.10 | |
| 19 | Olealkonium chloride | 5.76 | 0.34 | 0.31 |
| 20 | Olealkonium chloride | 5.81 | 0.29 | |
| 21 | Stearamidopropyl dimethylamine lactate | 6.22 | −0.12 | −0.04 |
| 22 | Stearamidopropyl dimethylamine lactate | 6.05 | 0.05 | |
| 23 | Cinnamidopropyl trimethyl-ammonium chloride | 5.98 | 0.12 | 0.05 |
| 24 | Cinnamidopropyl trimethyl-ammonium chloride | 6.12 | −0.02 | |
| 25 | Stearalkonium chloride | 5.93 | 0.17 | 0.25 |
| 26 | Stearalkonium chloride | 5.77 | 0.33 | |
| 27 | Behenalkonium chloride | 1.60 | 4.50 | 4.41 |
| 28 | Behenalkonium chloride | 1.78 | 4.32 | |
| 29 | Behentrimonium chloride | 5.78 | 0.32 | 0.33 |
| 30 | Behentrimonium chloride | 5.76 | 0.34 | |
| 31 | Glyceryl caprate | 5.17 | 0.93 | 0.92 |
| 32 | Glyceryl caprate | 5.19 | 0.91 | |
| 33 | Sodium Coco PG-Dimonium chloride phosphate | 5.69 | 0.41 | 0.40 |
| 34 | Sodium Coco PG-Dimonium chloride phosphate | 5.71 | 0.39 | |

As illustrated in the above Table V, the quaternary ammonium compounds behentrimonium methosulfate and behenalkonium chloride containing compositions exhibited excellent log reduction values and antimicrobial activity against the microbe *Serratia Marcescens*. The other quaternary ammonium compound containing compositions tested exhibited little or no antimicrobial activity. As evident from the table, the activity is unexpected.

In accordance with the patent statutes, the best mode and preferred embodiment have been set forth, the scope of the invention is not limited thereto, but rather by the scope of the attached claims.

What is claimed is:

1. A composition having antimicrobial properties, comprising:
   an aliphatic alcohol having from 1 to about 8 carbon atoms in an amount from about 30 to less than 60 parts;
   an aromatic alcohol in an amount from about 0.5 to about 5.0 parts, wherein the aromatic alcohol is one or more of phenoxyethanol, benzyl alcohol, and 1-phenoxy-2-propanol;
   a cationic substrate binding activity enhancing substance in an amount from about 0.0125 to about 0.5 part, wherein the cationic substrate binding activity enhancing substance is behenoyl PG-trimonium chloride, behenamidopropyl PG-dimonium chloride, or a combination thereof; and
   water in an amount from about 33 to about 65 parts, all said parts based on 100 parts by weight of the composition, said composition free of a cationic cellulose polymer, and wherein the composition has a viscosity of from about 10 to about 100,000 centipoise.

2. The composition according to claim 1, wherein the aliphatic alcohol is present in an amount from about 45 to less than 60 parts, and wherein the aromatic alcohol is present in an amount from 0.75 to about 3.5 parts.

3. The composition according to claim 2, wherein the water is present in an amount from about 33 to about 50 parts, and wherein the cationic substrate binding activity enhancing substance is present in an amount from 0.03 to about 0.1 part.

4. The composition according to claim 3, wherein the composition further includes a non-ionic thickener.

5. The composition according to claim 2, wherein said aliphatic alcohol is methanol, ethanol, n-propanol, isopropyl alcohol, 2-methyl-2 propanol, hexanol, or combinations thereof.

6. The composition according to claim 5, wherein said aliphatic alcohol is present in an amount from about 50 to about 55 parts, and wherein said aromatic alcohol is present in an amount from about 1.0 to about 2.5 parts, and wherein said cationic substrate binding activity enhancing substance is present in an amount from about 0.04 to about 0.075 part.

7. The composition according to claim 6, wherein the aliphatic alcohol is propanol, isopropyl alcohol, or ethanol, or combinations thereof.

8. The composition according to claim 4, wherein the non-ionic thickener is a cellulose-based thickener in an amount from about 0.1 to about 3.0 parts.

9. The composition according to claim 8, wherein the composition further includes a polyol, a skin conditioner, or pH adjusters or combinations thereof.

10. The composition according to claim 9, wherein the viscosity of the composition is 30 to about 120 centipoise, wherein the thickener comprises 2-hydroxypropyl cellulose, and wherein water is present in an amount from about 35 to about 45 parts.

11. A method for forming an antimicrobial composition, comprising the steps of:
providing from 33 to about 65 parts of water to a vessel;
adding a cationic substrate binding activity enhancing substance to the vessel in an amount from about 0.0125 to about 0.5 part, wherein the cationic substrate binding activity enhancing substance is behenoyl PG-trimonium chloride, behenamidopropyl PG-dimonium chloride, or a combination thereof;
adding an aromatic alcohol to the vessel in an amount from about 0.5 to about 5.0 parts, wherein the aromatic alcohol is one or more of phenoxyethanol, 1-phenoxy-2-propanol, and benzyl alcohol;
adding an aliphatic alcohol having from 1 to about 8 carbon atoms to the vessel in an amount from about 30 to about 58 parts;
adding a non-ionic thickener to the vessel; and
mixing the composition in the vessel, wherein the parts are based on 100 parts by weight of the composition, and wherein the composition is free of a cationic thickener.

12. The method according to claim 11, wherein the composition has a viscosity of from about 10 to about 100,000 centipoise, and wherein said aliphatic alcohol is methanol, ethanol, n-propanol, isopropyl alcohol, 2-methyl-2 propanol, hexanol, or combinations thereof.

13. The method according to claim 12, wherein the cationic substrate binding activity enhancing substance is present in an amount from about 0.03 to about 0.1 part, wherein said aromatic alcohol is present in an amount from about 0.75 to about 3.5 parts, and wherein the aliphatic alcohol is present in an amount from about 45 to about 58 parts.

14. The method according to claim 13, wherein the water is present in an amount from about 35 to about 50 parts.

15. The method according to claim 14, wherein the non-ionic thickener is a cellulose-based thickener in an amount from about 0.1 to about 3.0 parts, and wherein the composition further includes a polyol, a skin conditioner, pH adjusters or combinations thereof.

16. A composition having antimicrobial properties, comprising:
an aliphatic alcohol having from 1 to about 8 carbon atoms in an amount from about 30 to less than 60 parts;
an aromatic alcohol in an amount from about 0.5 to about 5.0 parts, wherein said aromatic alcohol is one or more of phenoxyethanol, 1-phenoxy-2-propanol, and benzyl alcohol;
a cationic substrate binding activity enhancing substance in an amount from about 0.0125 to about 0.5 part, wherein the cationic substrate binding activity enhancing substance is behenoyl PG-trimonium chloride, behenamidopropyl PG-dimonium chloride, or a combination thereof; and
water in an amount from about 33 to about 65 parts, all said parts based on 100 parts by weight of the composition, said composition free of a cationic cellulose polymer.

17. The composition according to claim 16, wherein the aliphatic alcohol is present in an amount from about 45 to less than 60 parts, and wherein the aromatic alcohol is present in an amount from 0.75 to about 3.5 parts, wherein the water is present in an amount from about 33 to about 50 parts, and wherein the cationic substrate binding activity enhancing substance is present in an amount from 0.03 to about 0.1 part.

18. The composition according to claim 17, wherein the composition further includes a non-ionic thickener.

19. The composition according to claim 17, wherein the composition has a viscosity of from about 10 to about 100,000 centipoise, and wherein said aliphatic alcohol is methanol, ethanol, n-propanol, isopropyl alcohol, 2-methyl-2 propanol, or hexanol, or combinations thereof, wherein said aliphatic alcohol is present in an amount from about 50 to about 55 parts, and wherein said aromatic alcohol is present in an amount from about 1.0 to about 2.5 parts, and wherein said cationic substrate binding activity enhancing substance is present in an amount from about 0.04 to about 0.075 part.

20. The composition according to claim 19, wherein the non-ionic thickener is a cellulose-based thickener in an amount from about 0.1 to about 3.0 parts, wherein the composition further includes a polyol, a skin conditioner, or pH adjusters or combinations thereof.

* * * * *